US00PP26907P3

(12) United States Plant Patent
Rat

(10) Patent No.: US PP26,907 P3
(45) Date of Patent: Jul. 5, 2016

(54) ***PAEONIA* PLANT NAMED 'RTPIV790-01'**

(50) Latin Name: ***Paeonia lactiflora*×P. *lutea***
Varietal Denomination: RTPIV790-01

(71) Applicant: Thierry Rat, Moissac (FR)

(72) Inventor: Thierry Rat, Moissac (FR)

(73) Assignee: Planteck (CA)

( * ) Notice: Subject to any disclaimer, the term of this patent is extended or adjusted under 35 U.S.C. 154(b) by 276 days.

(21) Appl. No.: 13/998,812

(22) Filed: Dec. 9, 2013

(65) Prior Publication Data

US 2015/0163980 P1 Jun. 11, 2015

(51) Int. Cl.
*A01H 5/02* (2006.01)

(52) U.S. Cl.
USPC ..... Plt./316

(58) Field of Classification Search
USPC ..... Plt./316
See application file for complete search history.

(56) References Cited

PUBLICATIONS

*Paeonien* Seiten. *Paeonia* 'Golden Isles' (*lutea* hybrids) 2001, retrieved on Nov. 5, 2015, retrieved from the Internet at <http://www.paeonia.ch/db/seiten_e/seite.php?id=44> 2 pp.*

* cited by examiner

*Primary Examiner* — June Hwu
(74) *Attorney, Agent, or Firm* — Cassandra Bright

(57) ABSTRACT

A new and distinct *Paeonia* cultivar named 'RTPIV790-01' is disclosed, characterized by distinctive bright yellow, fully double, strongly fragrant flowers. Plants are vigorous, symmetrical with strong stems holding flowers above foliage, and with attractive foliage through the Fall. The new cultivar is a *Paeonia*, suitable for ornamental garden purposes.

1 Drawing Sheet

Latin name of the genus and species: *Paeonia lactiflora*×*P. lutea*.

Variety denomination: 'RTPIV790-01'.

BACKGROUND OF THE INVENTION

The new cultivar is a product of a breeder program conducted by the inventor, Thierry Rat. This new variety, hereinafter referred to as 'RTPIV790-01', was discovered as part of a planned breeding program. The inventor, Thierry Rat crossed the seed parent *Paeonia lactiflora* 'Miss America', unpatented with the pollen parent, *Paeonia lutea* 'Golden Isles, unpatented,' during May of 2006. The resulting new variety was selected in a research nursery in Castel Sarrasin France during May of 2011.

After identifying the new variety as a potentially interesting selection, the inventor first organized propagation of 'RTPIV790-01' by shoot tissue culture at a commercial laboratory in L'Assomption, Quebec, during September of 2011. The inventor continued controlled testing and propagation, assessing stability of the unique characteristics of this variety. Several generations have been reproduced and have shown that the unique features of this cultivar are stable and reproduced true to type.

SUMMARY OF THE INVENTION

The cultivar 'RTPIV790-01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'RTPIV790-01' These characteristics in combination distinguish 'RTPIV790-01' as a new and distinct *Paeonia* cultivar:

1. Strong stems which hold the flowers uniquely erect and above the foliage.
2. Unique bright yellow, fully double flower.
3. Symmetrical, bushy plant shape.
4. Attractive foliage through Fall.
5. Strong fragrance to flower.

COMPARISON TO PARENT VARIETY

'RTPIV790-01' is similar in most horticultural characteristics to the seed parent variety *Paeonia lactiflora* 'Miss America'. Plants of the new cultivar 'RTPIV790-01' however, differ in the following characteristics:

1. 'Miss America' has a white, semi-double flowers, the new variety has a bright yellow, fully double flower.
2. The new variety has stronger stems.
3. Foliage of the new variety is more finely cut.

'RTPIV790-01' is similar in most horticultural characteristics to the pollen parent variety *Paeonia lutea* 'Golden Isles'. Plants of the new cultivar 'RTPIV790-01' however, differ in the following characteristics:

1. 'Golden Isles' has a yellow semi-double flowers, the new variety has a lighter yellow, fully double flower.
2. The new variety is a more herbaceous plant.
3. The new variety is more Winter hardy.

COMMERCIAL COMPARISON

'RTPIV790-01' can be compared to the commercial variety *Paeonia* 'Bartzella' unpatented. Plants of the new cultivar 'RTPIV790-01' are similar to plants of 'Bartzella' in most horticultural characteristics, as both are interspecific hybrid Peonies. Plants of the new cultivar 'RTPIV790-01' however, produce flowers, with a less pronounced red center. Additionally, flowers of the new variety are more fragrant, larger, with many more petals than flowers of 'Bartzella'. Plants of the new variety produce more secondary flower buds than plants of 'Barzella'.

'RTPIV790-01' can be compared to the commercial variety *Paeonia* 'Morning Lilac' unpatented. Plants of the new cultivar 'RTPIV790-01' are similar to plants of 'Morning Lilac' in most horticultural characteristics, as both are interspecific hybrid Peonies. Plants of the new cultivar 'RTPIV790-01' however, produce fully double, bright yellow flowers, whereas flowers of 'Morning Lilac' are dark purple in color, with significantly less petals. Additionally, plants of the new variety have more secondary flower buds then 'Morning Lilac' plants.

BRIEF DESCRIPTION OF THE PHOTOGRAPH

The accompanying photograph in FIG. 1 illustrates in full color a typical plant of 'RTPIV790-01' grown outdoors in Moissac, France. The plant is approximately 6 years old.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RTPIV790-01' plants grown outdoors in Moissac, France. Plants are approximately 1 year old, in a 2 gallon nursery container. Measurements and numerical values represent averages of typical plant types.

Botanical classification: *Paeonia lactiflora*×*P. lutea* 'RTPIV790-01'.

PROPAGATION

Typically by shoot tissue culture.

Root description: Freely branching storage root with numerous feeder roots.

PLANT

Growth habit: Compact and vigorous perennial herbaceous shrub. Symmetrical and rounded growth habit.

Height: Approximately 75 to 80 cm.

Plant spread: Approximately 85 cm.

Stems:

- *Length*.—Approximately 75 to 80 cm.
- *Diameter*.—Average 1 cm measured between first and second leaf.
- *Strength*.—Strong.
- *Internode length*.—Average 10 cm, highly variable.

Color: Near RHS Yellow-Green 144A.

Texture: Glabrous.

Age of plant described: Approximately 6 years.

FOLIAGE

Leaf: Alternate, bipinnately compound, with an overall ovate shape, which is wider than long. Average leaf 27 cm long and 40 cm wide. Erect attitude.

Leaflets:

- *Shape*.—Broadly elliptic.
- *Quantity and arrangement*.—3 primary leaflet further divided into secondary leaflets of variable number and form All leaflets sessile. Average 3 to 5 secondary leaflets.
- *Average length*.—Central leaflet average 16 cm.
- *Average width*.—Central leaflet average 16 cm.

Individual leaflet blades:

- *Shape of blade*.—Broad elliptic, variably incised.
- *Apex*.—Broadly acuminate, often with emargination.
- *Base*.—Attenuate.
- *Margin*.—Deeply incised.
- *Texture of top surface*.—Glabrous.
- *Texture of bottom surface*.—Glabrous.
- *Appearance of top surface*.—Matte.
- *Appearance of bottom surface*.—Matte.
- *Aspect*.—Flat to very minutely reflexed downward.
- *Color*.—Upper side: Near RHS Yellow-Green 147A. Under side: Near RHS Greyed-Green 191A.
- *Venation*.—Type: Pinnate. Venation color upper side: Near RHS Yellow-Green 145A. Venation color under side: Near RHS Yellow-Green 145A.
- *Petiole*.—Length: Average 6.5 cm. Diameter: 0.6 cm. Color: Near RHS Yellow-Green 144A. Texture: Glabrous, moderately glossy.

FLOWER

Natural flowering season: Flowers open approximately 60 days after bud break in early Spring. Flowering extends over a period of 4 to 6 weeks.

Inflorescence type and habit: Single, terminal or axilliary flowers, fully double, irregularly rounded with tight petal whorl. Erect flower attitude.

Flower longevity on plant: Approximately 8 to 12 days on the plant.

Quantity of flowers: 2-3 per stem.

Flower size:

- *Diameter*.—Approximately 16 to 17 cm.
- *Depth*.—Approximately 10 cm. (Flower height).

Peduncle:

- *Length*.—Approximately 23 cm.
- *Diameter*.—Approximately 0.7 cm.
- *Color*.—Near RHS Yellow-Green 144A.
- *Strength*.—Strong.
- *Texture*.—Glabrous.

Petals:

- *Petal arrangement*.—Tight, irregular whorl of 100 to 120 petals and petaloids.
- *Size*.—Length: Approximately 8 cm. Width: Approximately 6 cm.
- *Shape*.—Obovate.
- *Margin*.—Entire to sinuate.
- *Apex*.—Typically emarginate.
- *Base*.—Obtuse.
- *Texture*.—Smooth, glabrous all surfaces.
- *Aspect*.—Slightly ruffled, undulate.

Color:

*Petals*.—When opening: Upper surface: Near RHS Yellow 4A and 4B, base Red 42A. Lower surface: Near RHS Yellow 4A and 4B, base Red 42A. Fully opened: Upper surface: Near RHS Yellow 4A and 4B, covered in Red 42A, creating a very bright base Red 42A. Lower surface: Near RHS Yellow 4A and 4B, base Red 42A.

Petaloids:

*Type*.—Stamenoidal.

*Quantity*.—Average 10 to 30, variable.

*Size*.—Length: Approximately 4.0 to 7.0 cm. Width: Approximately 0.5 to 1.0 cm.

*Color*.—Same as petals, near RHS Yellow 4A and 4B, base Red 42A.

Bud:

*Shape*.—Elongated globose.

*Length*.—Approximately 5 cm.

*Diameter*.—Approximately 3.5 cm.

*Color*.—Near RHS Yellow-Green 144A.

Sepals:

*Quantity*.—5; 2 smaller and 3 larger.

*Length*.—Approximately 3.0 cm.

*Width*.—Approximately 4.2 cm.

*Shape*.—Obcordate to obovate.

*Aspect*.—Cupped.

*Apex*.—Mucronate.

*Margin*.—Entire. Color Interior Surface: RHS Yellow-Green 144A. Exterior Surface: RHS Yellow-Green 144B.

*Texture*.—Glabrous.

Fragrance: Strong.

REPRODUCTIVE ORGANS

Stamens:

*Number*.—Approximately 10 fully developed.

*Filament length*.—Approximately 1.5 cm.

*Filament color*.—Near RHS Red-Purple 60B.

Anthers:

*Length*.—1.3 cm.

*Shape*.—Elongated avoid.

*Color*.—Near RHS Yellow 6D.

*Pollen*.—Not observed to produce pollen.

Pistil:

*Type*.—Compound.

*Number*.—Average 6 carpels, variable.

*Carpel length*.—Approximately 2 to 2.5 cm.

*Stigma*.—Shape: Claw shaped, acutely convex. Color: Near RHS Yellow 3C.

*Ovary color*.—Near RHS Green 142D.

OTHER CHARACTERISTICS

Disease and pest resistance: Not observed to be susceptible nor resistant to normal diseases and pests of *Paeonia lactiflora*×*P. lutea*.

Temperature tolerance: Typically USDA Zones 3 to 9.

Fruit/seed production: Not observed.

What is claimed is:

1. A new and distinct cultivar of *Paeonia* plant named 'RTPIV790-01' as herein illustrated and described.

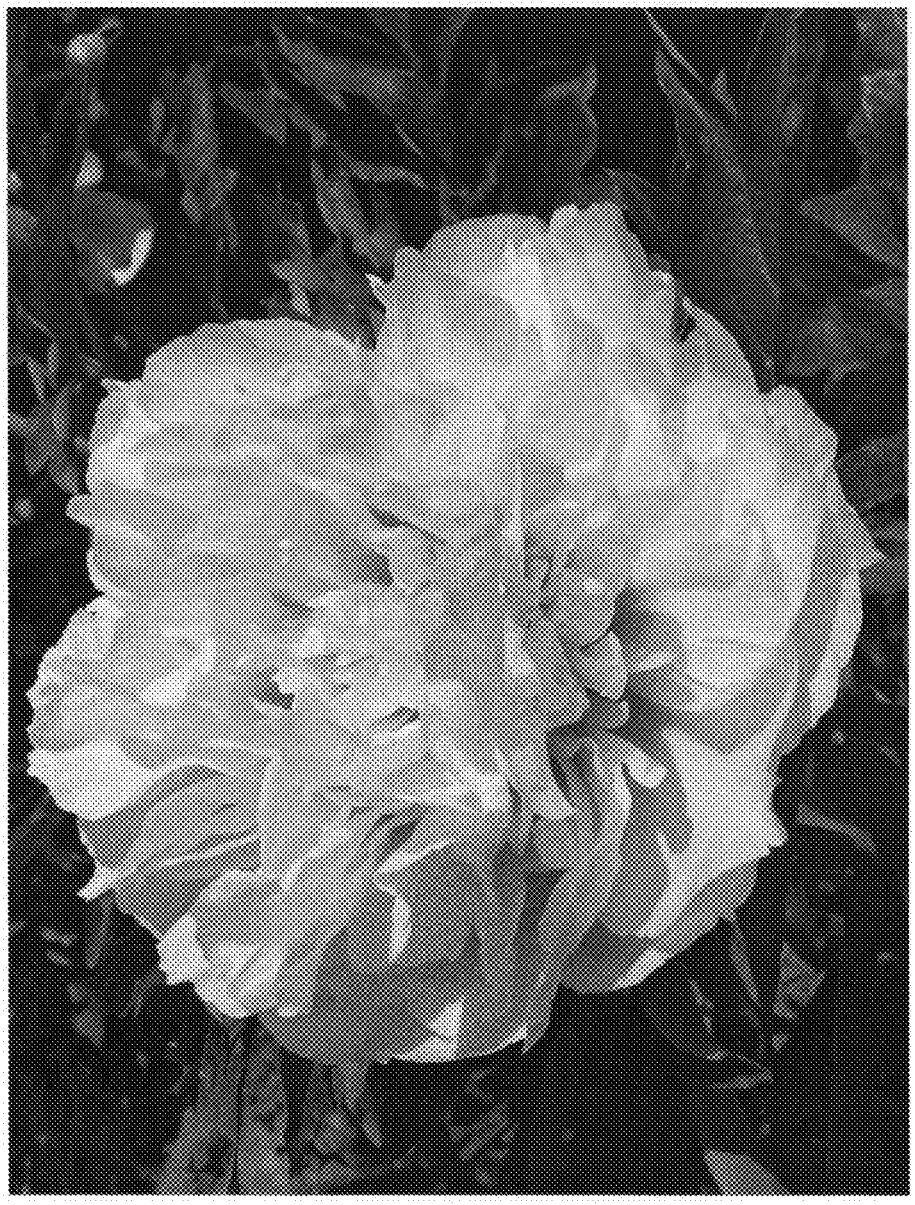

* * * * *